US012773498B2

(12) United States Patent
Jung et al.

(10) Patent No.: US 12,773,498 B2
(45) Date of Patent: Oct. 27, 2026

(54) SYRINGE CAPABLE OF REMOVING RESIDUAL PRESSURE

(71) Applicant: DXM.CO.,LTD., Hwasun-gun (KR)

(72) Inventors: Du Rok Jung, Hwasun-gun (KR); Kyoung Soo Shin, Goyang-si (KR)

(73) Assignee: DXM.CO., LTD., Jeollanam-do (KR)

( * ) Notice: Subject to any disclaimer, the term of this patent is extended or adjusted under 35 U.S.C. 154(b) by 349 days.

(21) Appl. No.: 18/689,580

(22) PCT Filed: Sep. 2, 2022

(86) PCT No.: PCT/KR2022/013209
§ 371 (c)(1),
(2) Date: Mar. 6, 2024

(87) PCT Pub. No.: WO2023/038372
PCT Pub. Date: Mar. 16, 2023

(65) Prior Publication Data
US 2025/0121138 A1 Apr. 17, 2025

(30) Foreign Application Priority Data
Sep. 9, 2021 (KR) ........................ 10-2021-0120365

(51) Int. Cl.
*A61M 5/315* (2006.01)

(52) U.S. Cl.
CPC ............................... *A61M 5/31511* (2013.01)

(58) Field of Classification Search
CPC .. A61M 5/31511; A61M 39/06; A61M 5/178; A61M 5/20; A61M 5/13515;
(Continued)

(56) References Cited

U.S. PATENT DOCUMENTS 5,782,803 A * 7/1998 Jentzen ................. A61M 5/347 604/218
2003/0035744 A1* 2/2003 Horita ................ A61M 5/31511 417/469
(Continued)

FOREIGN PATENT DOCUMENTS

GB 419556 A 11/1934
JP 2003135487 A 5/2003
(Continued)

OTHER PUBLICATIONS

European Search Report dated Sep. 26, 2024, in the counterpart European patent application No. 22867641.7.
(Continued)

*Primary Examiner* — Bhisma Mehta
*Assistant Examiner* — Marissa Taylor
(74) *Attorney, Agent, or Firm* — Rabin & Berdo, P.C.

(57) ABSTRACT

The present invention relates to a syringe capable of removing residual pressure, the syringe comprising: a barrel (110) which is filled with a medicinal material therein and has a chemical liquid discharge hole (113*c*) at one end thereof; a plunger (120) which is inserted into the barrel (110), moves forward by means of pressurization, and enables discharging of a chemical liquid through the chemical liquid discharge hole (113*c*), and in which a coupling shaft (122) protrudes from a front pressurizing plate (121) toward the chemical liquid discharge hole (113*c*) by a predetermined length; a gasket coupling ring (130) which is coupled to a rear end of the coupling shaft (122); and a residual pressure removing gasket (140) which is coupled to the gasket coupling ring (130) so as to surround the coupling shaft (122) from the front, and removes residual pressure thereinside when the pressure applied by the plunger (120) is released thereby preventing additional leakage of the chemical liquid,
(Continued)

wherein the gasket coupling ring (130) is coupled to the coupling shaft (122) to be spaced apart from the front pressurizing plate (121) of the plunger (120) by a reference distance, when the plunger (120) moves forward inside the barrel (110) by means of pressurization, the coupling shaft (122) pressurizes the inside of the residual pressure removing gasket (140) so that the front pressurizing plate (121) comes into contact with the gasket coupling ring (130) and moves forward, and the residual pressure removing gasket (140) includes: a fixing band (141) which is fitted to the gasket coupling ring (130) and is in close contact with an inner wall surface of the barrel (110); a tip cap (145) which surrounds the tip of the coupling shaft (122); and a slope transformable cap (143) which connects the fixing band (141) and the tip cap (145) at an angle, elastically extends when the plunger (120) is pressurized such that the tip cap (145) moves forward alongside the coupling shaft (122), contracts to an initial length when the pressure of the plunger (120) is released, and applies an elastic force such that the plunger (120) moves backward by the reference distance.

3 Claims, 7 Drawing Sheets

(58) Field of Classification Search
CPC ........ A61M 2005/3103; A61M 5/3221; A61M 5/344; A61M 2005/323; A61M 5/31513; A61M 2005/31516; A61M 5/31521; A61M 5/31523; A61M 2005/2086; A61M 2005/3143
See application file for complete search history.

(56) References Cited

U.S. PATENT DOCUMENTS

| | | | | |
|---|---|---|---|---|
| 2007/0135764 | A1 | 6/2007 | Chen | |
| 2008/0262439 | A1 | 10/2008 | Alheidt | |
| 2009/0247958 | A1 | 10/2009 | Carlyon | |
| 2010/0016807 | A1 | 1/2010 | Thilly | |
| 2015/0151056 | A1* | 6/2015 | Hung .................. | A61M 5/3221 604/218 |
| 2018/0117260 | A1* | 5/2018 | Shluzas ................. | A61M 5/178 |
| 2018/0169344 | A1 | 6/2018 | Arand et al. | |

FOREIGN PATENT DOCUMENTS

| | | | |
|---|---|---|---|
| JP | 2007-267907 | A | 10/2007 |
| JP | 2007-268189 | A | 10/2007 |
| JP | 2010523162 | A | 7/2010 |
| KR | 10-2005-0010398 | A | 1/2005 |
| KR | 10-2010-0053732 | A | 5/2010 |
| KR | 10-2011-0051562 | A | 5/2011 |
| KR | 10-2011-0095399 | A | 8/2011 |
| KR | 10-1234057 | B1 | 2/2013 |
| KR | 10-1696337 | B1 | 1/2017 |
| KR | 10-1776675 | B1 | 9/2017 |
| KR | 10-2000669 | B1 | 7/2019 |
| KR | 10-2019-0125293 | A | 11/2019 |
| KR | 10-2021-0046397 | A | 4/2021 |
| KR | 20-0493963 | Y1 | 7/2021 |
| KR | 10-2022-0130821 | A | 9/2022 |

OTHER PUBLICATIONS

International Search Report for PCT/KR2022/013209, mailed on Dec. 2, 2022.

* cited by examiner

SYRINGE CAPABLE OF REMOVING RESIDUAL PRESSURE

TECHNICAL FIELD

The present invention relates to a syringe, and more particularly, to a syringe capable of removing residual pressure applied to a plunger after pressure applied to the plunger in order to discharge a chemical liquid is released, thereby preventing leakage of the chemical liquid.

BACKGROUND ART

Syringes are widely used for medical or industrial purposes. Medical syringes are used to inject a medical liquid into patients, and industrial syringes are used to discharge a chemical such as an industrial glue in a predetermined amount.

FIG. 1 is a view showing an exemplary configuration of a conventional syringe 10. As shown, the conventional syringe 10 includes a barrel 11 in which a chemical liquid A is contained, a plunger 15 configured to move forward in the barrel 11, and a nozzle 13 coupled to a tip of the barrel 11 to discharge the chemical liquid therethrough.

In the conventional syringe 10, when a user manually pushes and presses the plunger 15, the plunger 15 moves forward in the barrel 11 to discharge the chemical liquid A through the nozzle 13. Then, when the pressure applied to the plunger 15 is released, discharge of the chemical liquid A stops.

However, in the conventional syringe 10, when the pressure manually applied to the plunger 15 is released, residual pressure is present therein, which causes the plunger 15 to move forward, thus incurring a problem that the chemical liquid A slightly leaks from the nozzle 13.

DISCLOSURE

Technical Problem

The present invention has been made to solve the above-described problem, and an object of the present invention is to provide a syringe capable of removing residual pressure present therein after pressure applied to a plunger is released, thereby preventing additional leakage of a chemical liquid.

The above object and various advantages of the present invention will become more apparent to those skilled in the art from preferred embodiments of the present invention.

Technical Solution

The object of the present invention may be accomplished by a syringe capable of removing residual pressure. The syringe of the present invention includes a barrel (110) configured to contain a chemical liquid therein and including a chemical liquid discharge hole (113*c*) formed in an end thereof, a plunger (120) inserted into the barrel (110), configured to move forward when pressed to allow the chemical liquid to be discharged through the chemical liquid discharge hole (113*c*), and including a front pressing plate (121) formed at a front side thereof and a coupling shaft (122) protruding from the front pressing plate (121) by a predetermined length toward the chemical liquid discharge hole (113*c*), a gasket coupling ring (130) coupled to a rear end of the coupling shaft (122), and a residual pressure removing gasket (140) coupled to the gasket coupling ring (130) so as to surround the coupling shaft (122) from the front and configured to remove inner residual pressure in order to prevent additional leakage of the chemical liquid when pressure applied to the plunger (120) is released, wherein the gasket coupling ring (130) is coupled to the coupling shaft (122) so as to be spaced apart from the front pressing plate (121) of the plunger (120) by a reference distance. When the plunger (120) is pressed and moves forward in the barrel (110), the front pressing plate (121) comes into contact with the gasket coupling ring (130), and the coupling shaft (122) moves forward while pressing an inner side of the residual pressure removing gasket (140). The residual pressure removing gasket (140) includes a fixing band (141) formed so as to be fitted to the gasket coupling ring (130) and to be in close contact with an inner wall surface of the barrel (110), a tip cap (145) surrounding a front end of the coupling shaft (122), and an inclined deformable cap (143) interconnecting the fixing band (141) and the tip cap (145) in an inclined state and configured to elastically extend and allow the tip cap (145) to move forward together with the coupling shaft (122) when the plunger (120) is pressed and to contract to an original length and apply elastic force to the plunger (120) so that the plunger (120) is moved backward by the reference distance when pressure applied to the plunger (120) is released.

According to an embodiment, the gasket coupling ring (130) may include a ring body (131) fitted on the coupling shaft (122), a rear flange (135) protruding from an outer circumference of a rear end of the ring body (131) and spaced apart from the front pressing plate (121) by the reference distance, and a front flange (133) protruding from an outer circumference of a front end of the ring body (131) to a lower height than the rear flange (135) and forming a band fitting groove (137) into which the fixing band (141) is fitted between the front flange (133) and the rear flange (135). The coupling shaft (122) may be provided with a movement limiting protrusion (123) protruding therefrom so as to be in contact with the front flange (133) to limit forward movement of the gasket coupling ring (130).

According to an embodiment, the tip cap (145) may be formed to have a length allowing the front end of the coupling shaft (122) to be exposed to the outside, and the syringe may further include a tip separation preventing protrusion (124) provided in a coupling region between the tip cap (145) and the coupling shaft (122) so as to fix the position of the tip cap (145).

Advantageous Effects

The syringe according to the present invention is configured such that a coupling shaft protrudes from a front end of a plunger and a gasket coupling ring and a residual pressure removing gasket are coupled to the coupling shaft. When the plunger is pressed, the residual pressure removing gasket is elastically increased in length, and when pressure applied to the plunger is released, the residual pressure removing gasket is restored to the original length and applies elastic force to the plunger, whereby the plunger is moved backward by a reference distance and thus inner residual pressure is removed.

Accordingly, it is possible to effectively solve the problem with the conventional syringe in which, when pressure applied thereto is released, a chemical liquid contained therein slightly leaks due to residual pressure.

BEST MODEL

Figure 1:
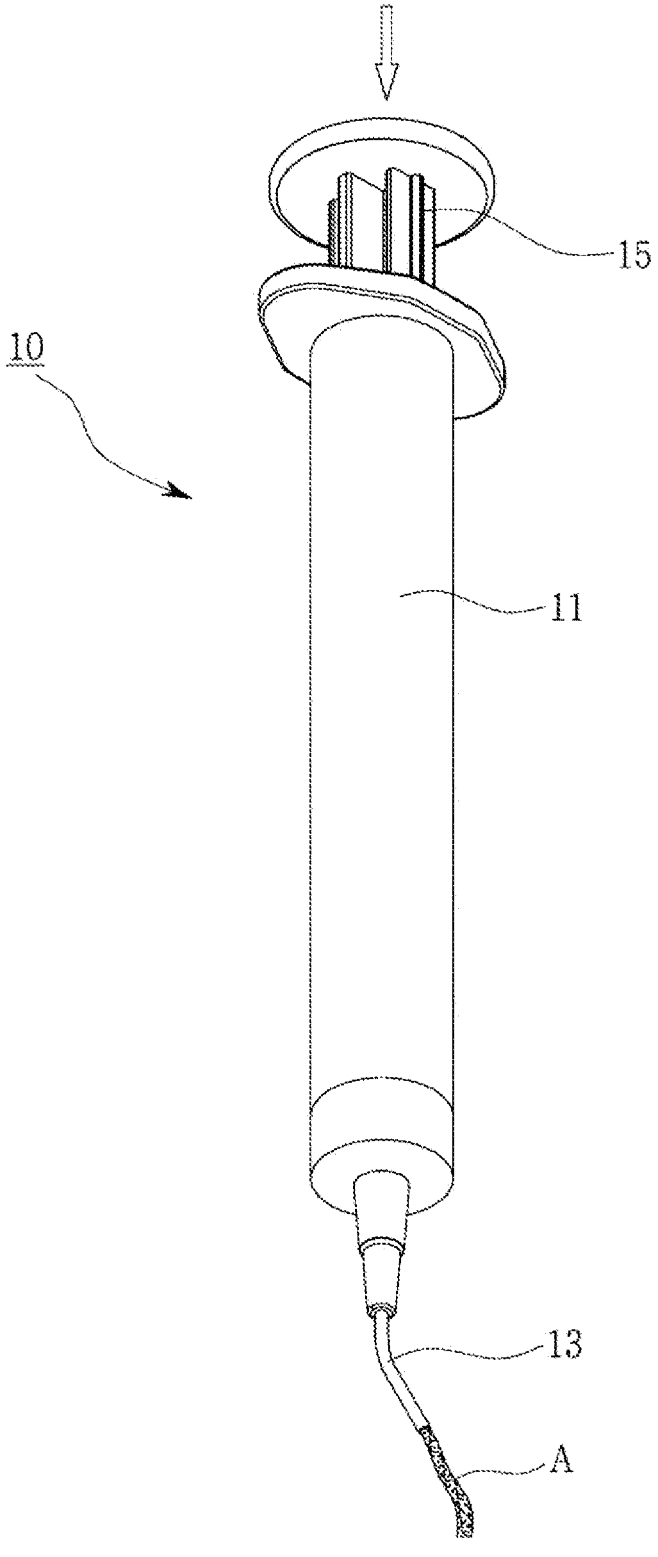
FIG. 1 is a view showing an exemplary configuration of a conventional syringe.

For better understanding of the present invention, preferred embodiments of the present invention will be described with reference to the accompanying drawings. The embodiments of the present invention can be modified in various forms, and the scope of the present invention should not be construed as being limited to the embodiments described in detail below. The embodiments are provided so that those of ordinary skill in the art can completely understand the present invention. Therefore, the shapes and the like of the components in the drawings can be exaggerated so as to emphasize a clearer explanation. It should be noted that the same members are denoted by the same reference numerals in the drawings. A detailed description of known functions and configurations incorporated herein will be omitted when it may unnecessarily obscure the subject matter of the present invention.

Figure 2:
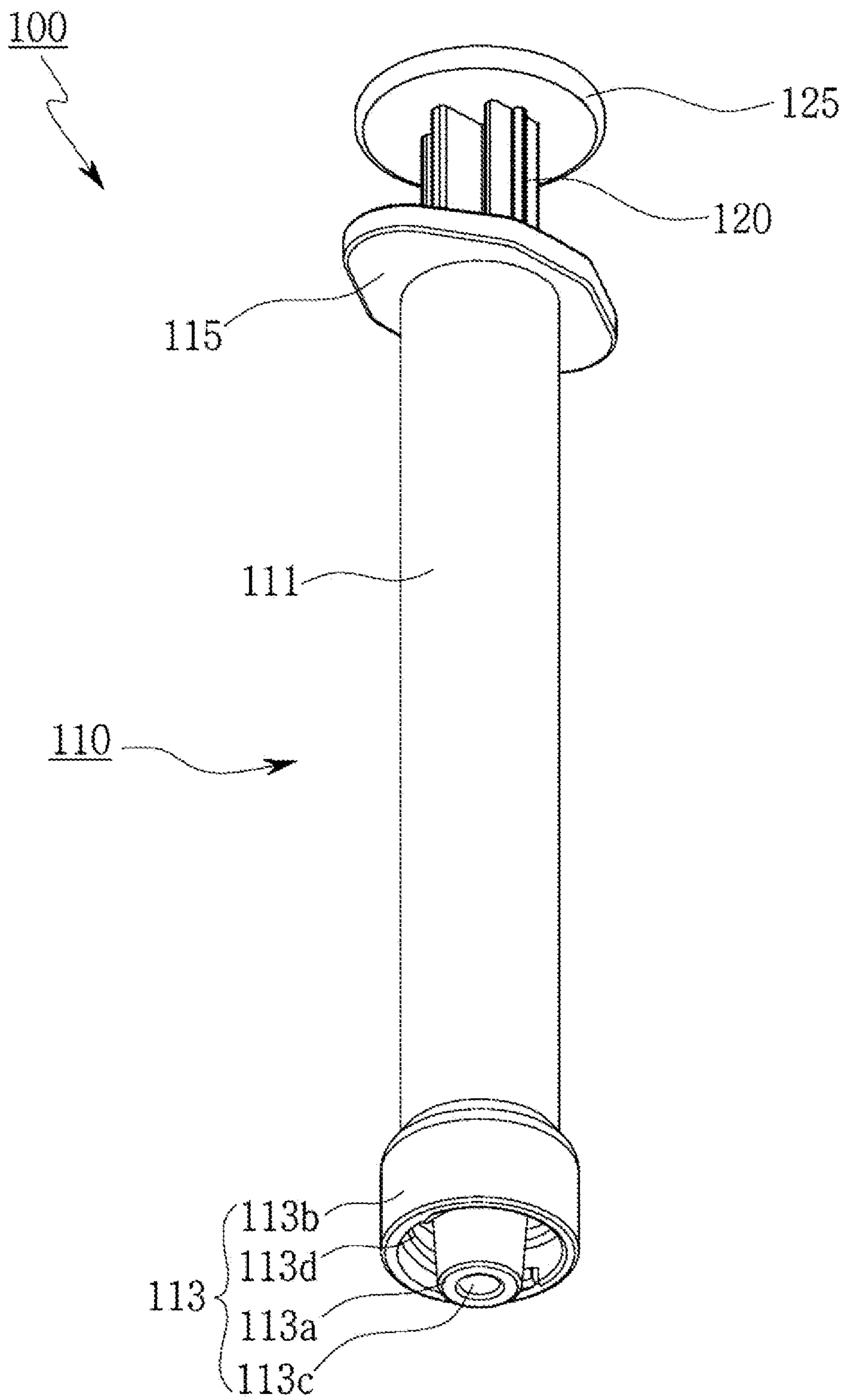
FIG. 2 is a perspective view showing the configuration of a syringe according to the present invention.
Figure 3:
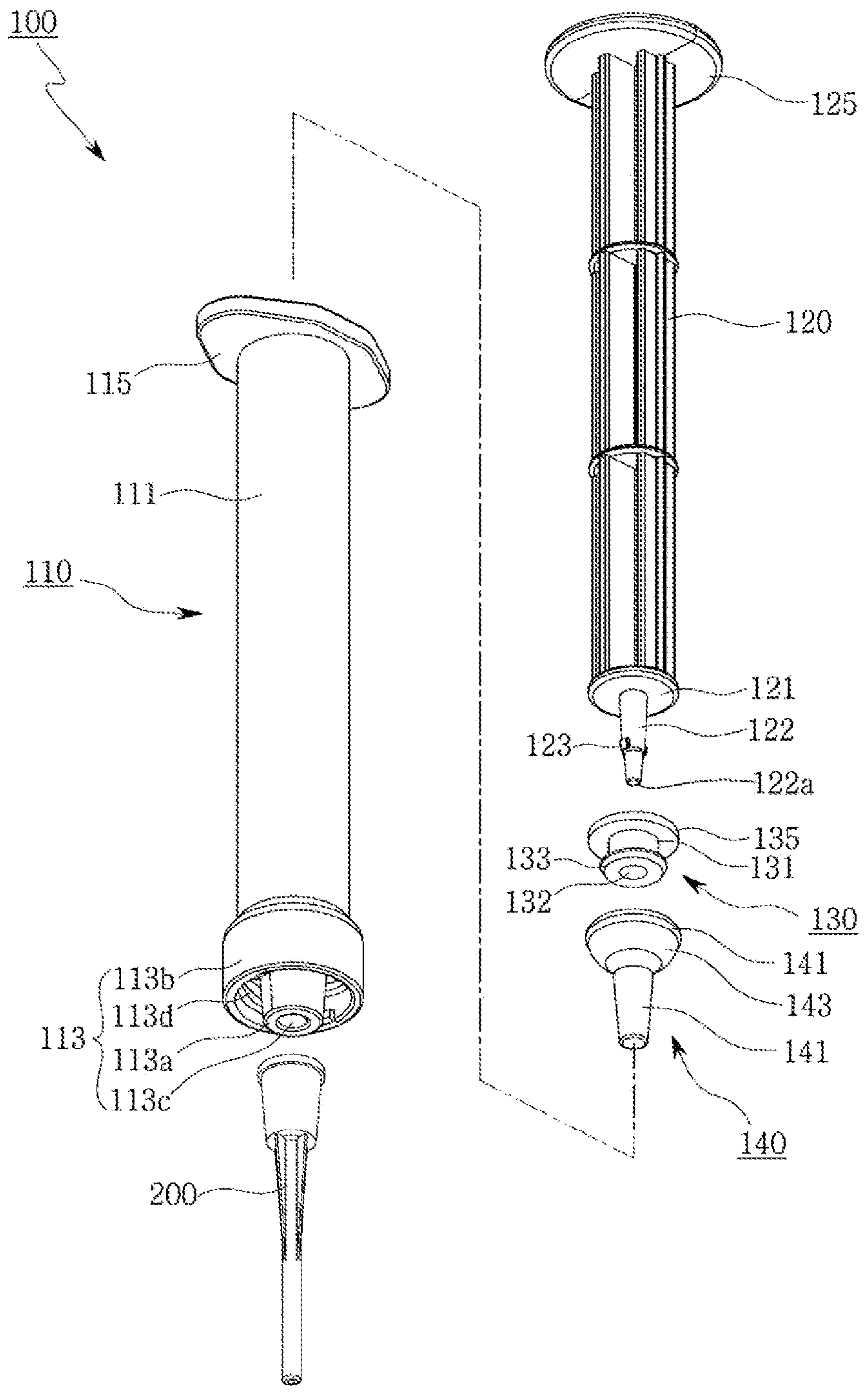
FIG. 3 is an exploded perspective view showing the configuration of the syringe according present invention.
Figure 4:
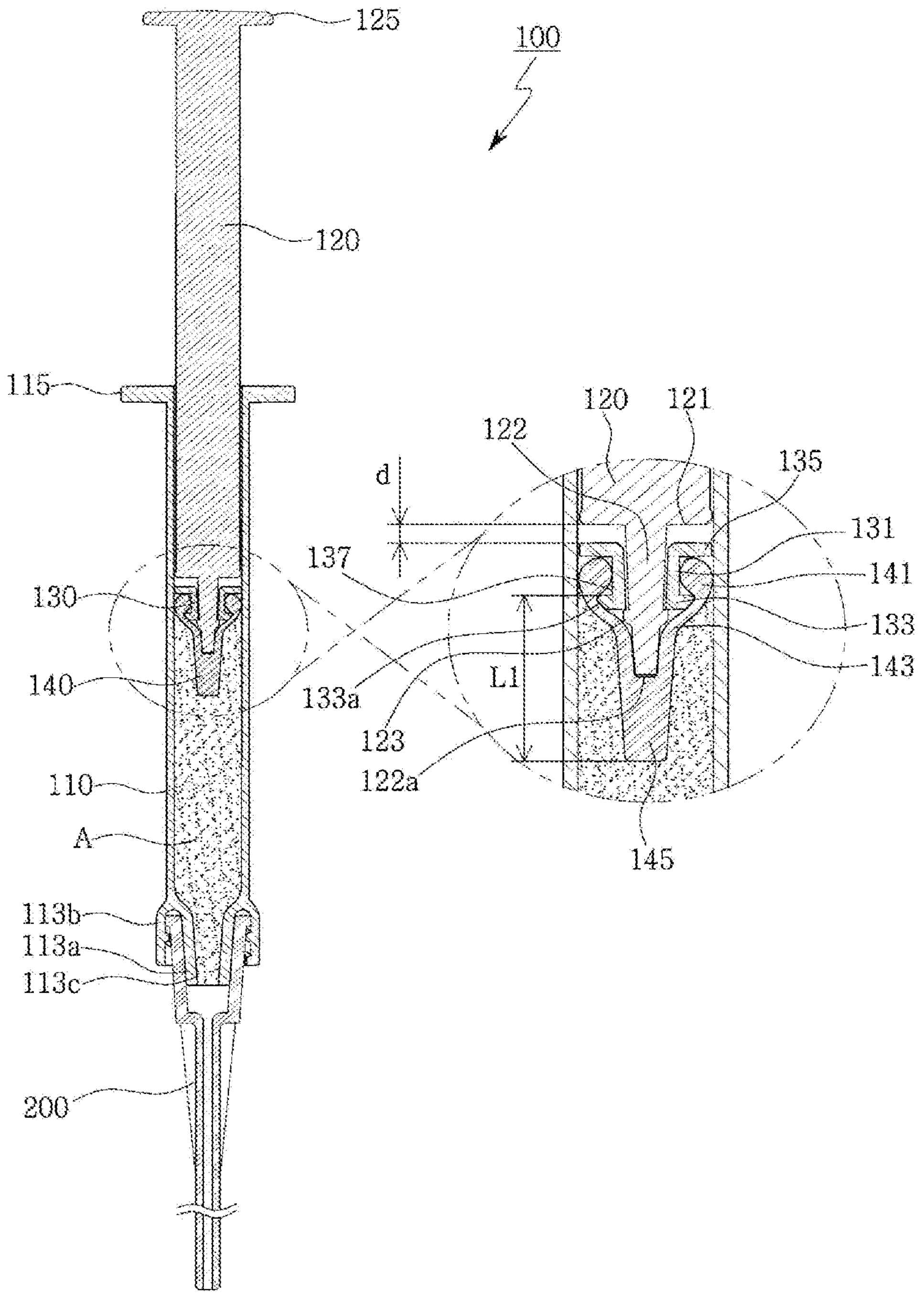
FIGS. 4 to 6 are cross-sectional views showing the operation process of the syringe according to the present invention.
Figure 5:
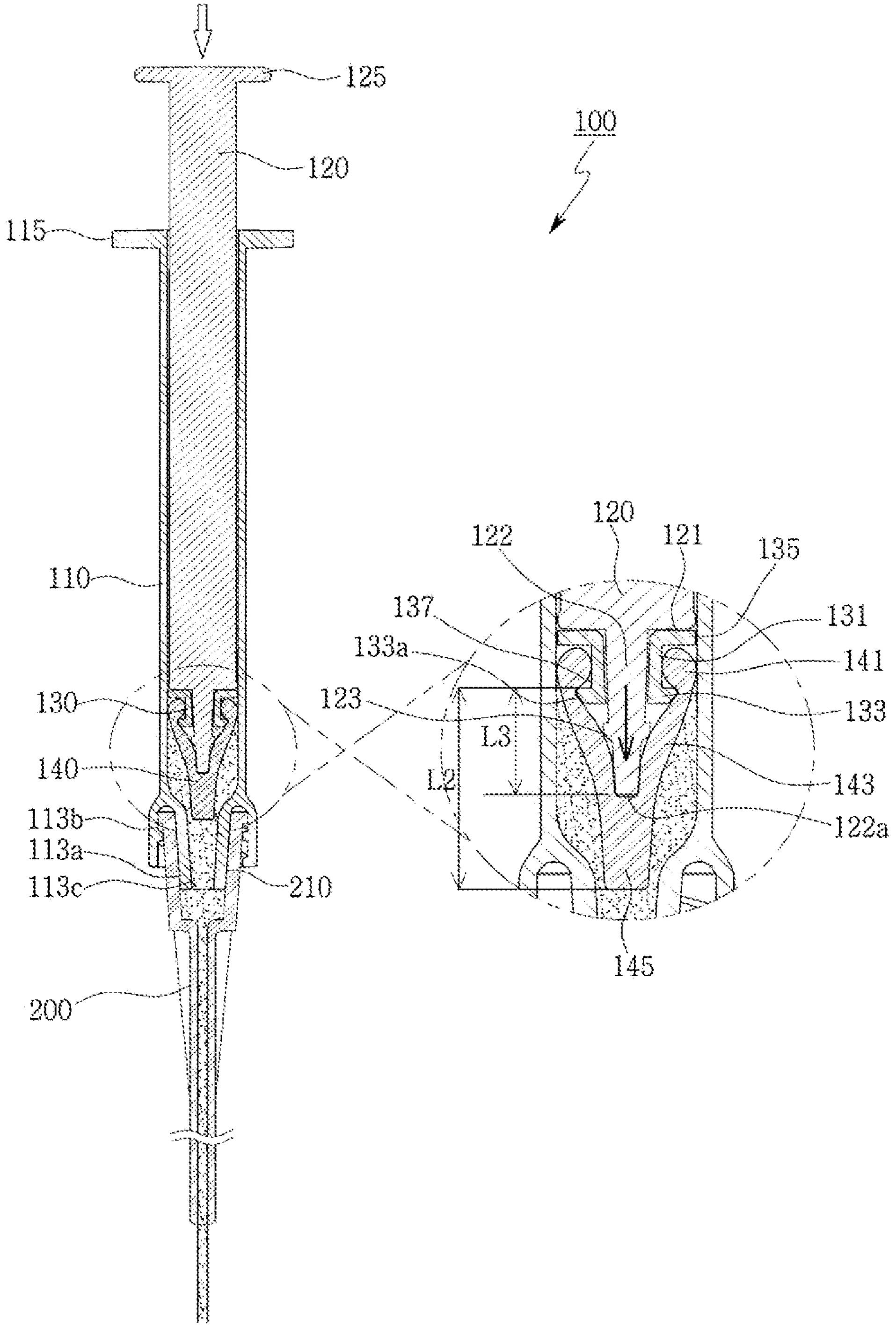
Figure 6:
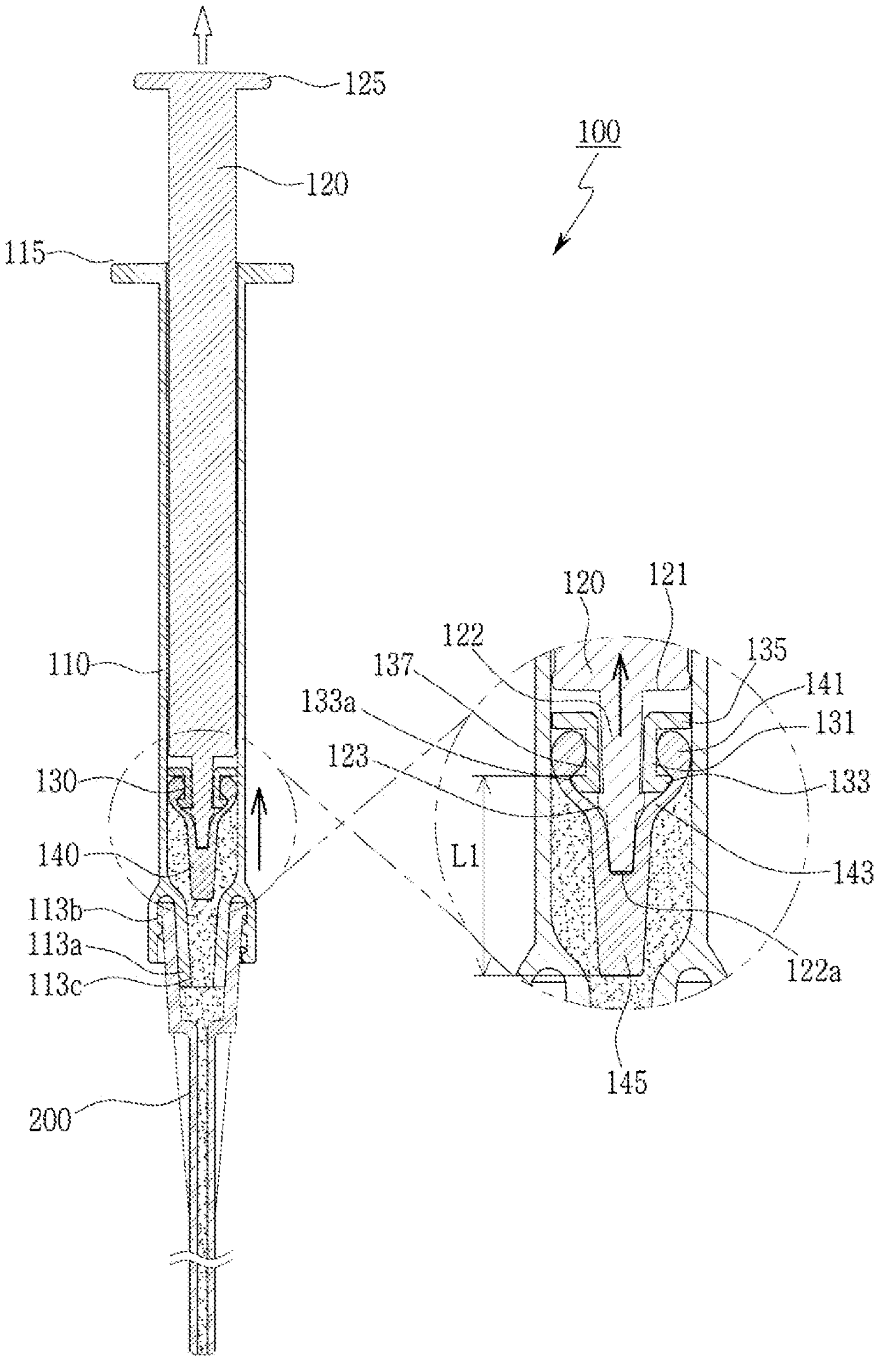

FIG. 2 is a perspective view showing the configuration of a syringe 100 according to the present invention, FIG. 3 is an exploded perspective view showing the configuration of the syringe 100, and FIGS. 4 to 6 are cross-sectional views showing the operation process of the syringe 100.

As shown in FIGS. 2 and 3, the syringe 100 of the present invention includes a barrel 110 in which a chemical liquid A is stored, a plunger 120 configured to move from the rear end of the barrel 110 toward the front end of the barrel 110 to pressurize the chemical liquid A so that the chemical liquid A is discharged, a gasket coupling ring 130 coupled to the front end of the plunger 120, and a residual pressure removing gasket 140 coupled to the front end of the plunger 120 via the gasket coupling ring 130 and configured to remove residual pressure by causing the plunger 120 to move backward by a reference distance when pressure applied to the plunger 120 is released.

The syringe 100 of the present invention is provided at the front end of the plunger 120 with the residual pressure removing gasket 140 that is elastically variable and allows the plunger 120, stopped by release of the pressure applied thereto, to be moved backward to a reference position by residual pressure. Accordingly, an effect of solving the conventional problem of continuous leakage of a chemical liquid due to residual pressure is obtained.

The barrel 110 stores the chemical liquid A therein and allows the chemical liquid A to be discharged by pressurization by the plunger 120. A nozzle 200 or an adapter (not shown), through which the chemical liquid A is discharged, is coupled to the front end of the barrel 110.

As shown in FIGS. 3 and 4, the barrel 110 includes a barrel body 111 in which the chemical liquid is stored, a connection end 113 provided at the front end of the barrel body 111 so as to allow the nozzle 200 or the adapter to be detachably coupled thereto and having a chemical liquid discharge hole 113*c* formed therein, and a flange 115 provided at the rear end of the barrel body 111 so as to support movement of the plunger 120.

The connection end 113 includes an inner tube 113*a* in which the chemical liquid discharge hole 113*c* is formed and an outer tube 113*b* formed so as to be spaced a predetermined gap from the inner tube 113*a* to form a nozzle insertion recess 113*d* into which the nozzle 200 is inserted.

The plunger 120 is inserted into the barrel 110 through the rear end of the barrel 110 and is moved forward along the inner wall surface of the barrel 110 by the pressure applied thereto by the user, thereby pressurizing the chemical liquid A so that the chemical liquid A is discharged through the chemical liquid discharge hole 113*c*. The plunger 120 is formed in a shape of a bar having an outer diameter corresponding to the inner diameter of the barrel 110.

The plunger 120 is provided at the front end thereof with a front pressing plate 121 formed so as to be moved while pressurizing the chemical liquid and is provided at the rear end thereof with a rear pressing plate 125 formed so as to be pressed by the user. As shown in FIGS. 3 and 4, a coupling shaft 122, to which the residual pressure removing gasket 140 is coupled, is formed in the central region of the front pressing plate 121 so as to protrude by a predetermined length. The coupling shaft 122 is formed such that the outer diameter thereof is constant or gradually decreases in a direction approaching the front end 122*a* thereof, thereby facilitating coupling of the residual pressure removing gasket 140 thereto.

In the middle of the coupling shaft 122, a plurality of movement limiting protrusions 123 is formed so as to protrude from the peripheral surface of the coupling shaft 122 and to be spaced apart from each other at regular angular intervals. As shown in FIG. 4 in an enlarged manner, when the gasket coupling ring 130 is fitted on the coupling shaft 122, the movement limiting protrusions 123 contact and support the gasket coupling ring 130 so that the gasket coupling ring 130 is fixed in position without being pushed forward.

As shown in FIG. 4 in an enlarged manner, the movement limiting protrusions 123 are provided at a position spaced apart from the front pressing plate 121 by a distance equal to a sum of a reference distance d and the length of a ring body 131. Accordingly, when the gasket coupling ring 130 is coupled to the coupling shaft 122 so as to contact the movement limiting protrusions 123, the gasket coupling ring 130 is located so as to be spaced apart from the front pressing plate 121 by the reference distance d.

The gasket coupling ring 130 is fitted on the coupling shaft 122 to fix the position of the residual pressure removing gasket 140. The gasket coupling ring 130 is configured such that a ring body 131 formed in an elastic ring shape so as to be fitted on the coupling shaft 122, a front flange 133 protruding by a predetermined height from the front end of the ring body 131 in a radially outward direction, and a rear flange 135 protruding by a height corresponding to the inner diameter of the barrel 110 from the rear end of the ring body 131 in the radially outward direction are integrally formed with each other.

The ring body 131 is formed in a shape of a ring through which a shaft insertion hole 132, into which the coupling shaft 122 is inserted, is formed. The ring body 131 is formed of rubber or silicone, which is elastically expandable, or plastic. The front flange 133 and the rear flange 135 are formed perpendicularly at the front side and the rear side of the ring body 131, respectively, so as to extend in a circumferential direction. The rear flange 135 is formed to a height corresponding to the inner diameter of the barrel 110 so as to contact the inner wall surface of the barrel 110, thereby preventing the residual pressure removing gasket 140 from escaping during movement of the plunger 120 and preventing the chemical liquid A from moving in the reverse direction.

The front flange 133 is formed to be lower than the rear flange 135, and a band fitting groove 137 is formed between the front flange 133 and the rear flange 135. In addition, due to the height difference from the rear flange 135, the front flange 133 supports an inclined deformable cap 143 of the residual pressure removing gasket 140 so that the inclined deformable cap 143 surrounds the coupling shaft 122 and the gasket coupling ring 130 in an inclined state.

In this case, the front flange 133 is formed so as to gradually decrease in outer diameter in a direction from the rear side thereof toward the front side thereof to form an inclined surface 133*a* at a side portion thereof, thereby supporting the inner side of the inclined deformable cap 143 so that the inclined deformable cap 143 maintains a shape of gradually narrowing in a direction approaching the front end thereof.

The residual pressure removing gasket 140 is coupled to the gasket coupling ring 130 so as to surround the coupling shaft 122 and moves in the barrel 110 together with the plunger 120 to discharge the chemical liquid A. In addition, when the pressure applied to the plunger 120 is released, the residual pressure removing gasket 140 moves the plunger 120 backward by the standard distance to remove residual pressure applied to the plunger 120, thereby preventing additional leakage of the chemical liquid A.

The residual pressure removing gasket 140 includes a fixing band 141 fitted into the band fitting groove 137 in the gasket coupling ring 130, a tip cap 145 fitted on the coupling shaft 122 so as to surround the front end of the coupling shaft 122, and an inclined deformable cap 143 interconnecting the tip cap 145 and the fixing band 141 and formed to be elastically deformable so as to exert elastic force to cause the plunger 120 to move backward.

The tip cap 145, the inclined deformable cap 143, and the fixing band 141 are formed as an integrated structure made of an elastic material and having a closed front end and a rear end in which an insertion space, into which the coupling shaft 122 is inserted, is defined. The fixing band 141 of the residual pressure removing gasket 140 is first fitted on the coupling shaft 122 and then is pulled toward the gasket coupling ring 130 so that the coupling shaft 122 is inserted into the tip cap 145. Then, the pulled fixing band 141 is fitted into the band fitting groove 137 in the gasket coupling ring 130.

The fixing band 141 is formed to be thicker than the other portions and thus is elastically fitted into the band fitting groove 137 and fixed in position. The outer diameter surface of the fixing band 141 is in contact with the inner wall surface of the barrel 110, thereby preventing the chemical liquid A from moving in the reverse direction toward the plunger 120.

The tip cap 145 is formed to be long enough to surround a portion of the coupling shaft 122 from the movement limiting protrusions 123 to the front end 122*a* of the coupling shaft 122. The inclined deformable cap 143 connects the fixing band 141 to the tip cap 145 and is formed to be thinner than the fixing band 141 and the tip cap 145. Accordingly, the inclined deformable cap 143 is easily elastically deformed.

The inclined deformable cap 143 is supported by the inclined surface 133*a* of the front flange 133 and the movement limiting protrusions 123, and is gradually reduced in outer diameter in a direction from the rear side thereof toward the front side thereof to be connected to the tip cap 145. Depending on whether the user presses the plunger 120 in order to discharge the chemical liquid, the inclined deformable cap 143 allows the chemical liquid to be discharged or moves the plunger 120 backward to prevent additional discharge of the chemical liquid while being elastically deformed.

As shown in FIG. 4, in an initial state in which the plunger 120 is not pressed, the residual pressure removing gasket 140 fitted on the coupling shaft 122 is maintained in a state of being fixed in position by the fixing band 141 fitted to the gasket coupling ring 130. In this state, a portion from the inclined deformable cap 143 to the tip cap 145 maintains a first length L1. In addition, the front pressing plate 121 of the plunger 120 is maintained spaced apart from the rear flange 135 of the gasket coupling ring 130 by the reference distance d.

As shown in FIG. 5, when the user presses the rear pressing plate 125, the plunger 120 moves forward in the barrel 110. Accordingly, the front pressing plate 121 of the plunger 120 is pressed to move forward and is brought into contact with the rear flange 135, and the coupling shaft 122 also moves forward toward the tip cap 145 in the residual pressure removing gasket 140.

In this case, the inclined deformable cap 143 is elastically deformed by the moving distance of the coupling shaft 122, i.e., the reference distance d, and thus the length L3 thereof increases. A second length L2 from the inclined deformable cap 143 to the tip cap 145 becomes greater than the first length L1.

The plunger 120 moves forward with the residual pressure removing gasket 140 deformed to the second length L2, and the chemical liquid A is discharged to the outside through the nozzle 200.

When the plunger 120 reaches a position for discharge of a user's desired amount of chemical liquid, the user stops pressing the plunger 120. When the pressure applied to the plunger 120 is released, as shown in FIG. 6, the inclined deformable cap 143 elastically deformed to a greater length is restored to the original length and applies elastic force to the coupling shaft 122 received therein. Accordingly, as shown in FIG. 6 in an enlarged manner, the coupling shaft 122 and the plunger 120 are moved backward by the reference distance d, and the front pressing plate 121 is moved to a position spaced apart from the rear flange 135 by the reference distance d.

In this way, as the plunger 120 is moved backward by the reference distance d by the elastic force of the inclined deformable cap 143, the residual pressure applied to the plunger 120 is removed, whereby additional discharge of the chemical liquid through the nozzle 200 is prevented, and an accurate amount of chemical liquid is discharged.

Figure 7:
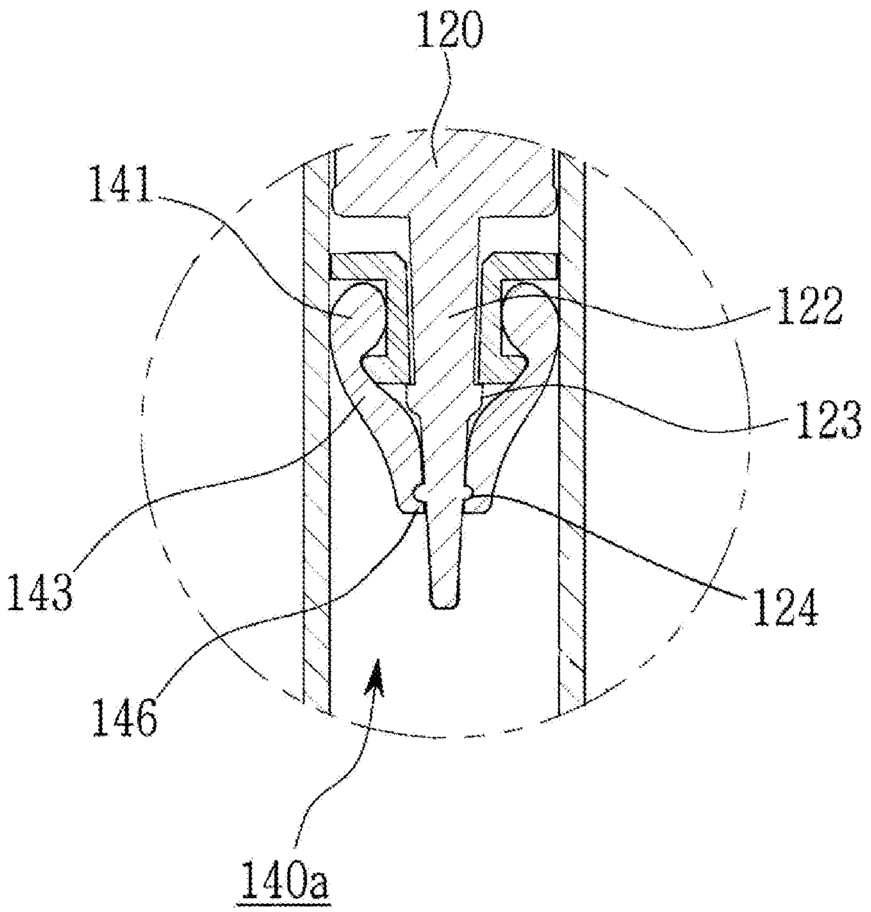
FIG. 7 is a view showing a modified example of a residual pressure removing gasket of the syringe of the present invention.

Meanwhile, FIG. 7 is a view showing a modified example of a residual pressure removing gasket 140*a* of the present invention. The residual pressure removing gasket 140 according to the preferred embodiment described above is configured such that the fixing band 141, the inclined deformable cap 143, and the tip cap 145 are integrally formed with each other.

However, this is merely given by way of example, and as shown in FIG. 7, a fixing band 141 and an inclined deformable cap 143 are integrally formed with each other and are fitted to the gasket coupling ring 130, and a tip cap 145 is formed to be short so as to expose the front end of the coupling shaft 122 to the outside.

In this case, an end portion of the tip cap 145 is formed to be thicker than the other portions thereof and is fixed in position by being caught by a tip separation preventing protrusion 124 protruding from the coupling shaft 122. This achieves sealing for prevention of backflow of the chemical liquid A.

Similarly, when pressure is applied to or released from the plunger 120, the inclined deformable cap 143 is elastically deformed so as to increase in length or to contract to the original length so that the plunger 120 is moved backward and residual pressure is removed.

As described above, the syringe according to the present invention is configured such that the coupling shaft protrudes from the front end of the plunger and the gasket coupling ring and the residual pressure removing gasket are coupled to the coupling shaft. When the plunger is pressed, the residual pressure removing gasket is elastically increased in length, and when the pressure applied to the plunger is released, the residual pressure removing gasket is restored to the original length and applies elastic force to plunger, whereby the plunger is moved backward by the reference distance and thus inner residual pressure is removed.

As a result, it is possible to effectively solve the problem with the conventional syringe in which, when pressure applied thereto is released, a chemical liquid contained therein slightly leaks due to residual pressure.

The embodiments of the syringe of the present invention described above are merely exemplary, and those skilled in the art will appreciate that various modifications and equivalent other embodiments are possible therefrom. Therefore, it will be understood that the present invention is not limited to the form mentioned in the above detailed description. Therefore, the true technical protection scope of the present invention will be defined by the technical spirit of the appended claims. It is also to be understood that the present invention includes all modifications, equivalents and substitutions within the spirit and scope of the invention as defined by the appended claims.

DESCRIPTION OF REFERENCE NUMERALS

100: syringe 110: barrel
111: barrel body 113: connection end
113*a*: inner tube 113*b*: outer tube
113*c*: chemical liquid discharge hole 113*d*: nozzle insertion recess
115: flange 120: plunger
121: front pressing plate 122: coupling shaft
122*a*: front end 123: movement limiting protrusion
124: tip separation preventing protrusion 125: rear pressing plate
130: gasket coupling ring 131: ring body
132: shaft insertion hole 133: front flange
133*a*: inclined surface 135: rear flange
137: band fitting groove 140: residual pressure removing gasket
141: fixing band 143: inclined deformable cap
145: tip cap 200: nozzle
A: chemical liquid

The invention claimed is:

1. A syringe capable of removing residual pressure, the syringe comprising:

a barrel (110) configured to contain a chemical liquid therein and comprising a chemical liquid discharge hole (113*c*) formed in an end thereof;

a plunger (120) inserted into the barrel (110), configured to move forward when pressed to allow the chemical liquid to be discharged through the chemical liquid discharge hole (113*c*), and comprising a front pressing plate (121) formed at a front side thereof and a coupling shaft (122) protruding from the front pressing plate (121) by a predetermined length toward the chemical liquid discharge hole (113*c*);

a gasket coupling ring (130) coupled to a rear end of the coupling shaft (122); and a residual pressure removing gasket (140) coupled to the gasket coupling ring (130) so as to surround the coupling shaft (122) from a front and configured to remove inner residual pressure in order to prevent additional leakage of the chemical liquid when pressure applied to the plunger (120) is released, wherein the gasket coupling ring (130) is coupled to the coupling shaft (122) so as to be spaced apart from the front pressing plate (121) of the plunger (120) by a reference distance, wherein, when the plunger (120) is pressed and moves forward in the barrel (110), the front pressing plate (121) comes into contact with the gasket coupling ring (130), and the coupling shaft (122) moves forward while pressing an inner side of the residual pressure removing gasket (140), and wherein the residual pressure removing gasket (140) comprises:

a fixing band (141) formed so as to be fitted to the gasket coupling ring (130) and to be in close contact with an inner wall surface of the barrel (110);

a tip cap (145) surrounding a front end of the coupling shaft (122); and an inclined deformable cap (143) interconnecting the fixing band (141) and the tip cap (145) in an inclined state and configured to elastically extend and allow the tip cap (145) to move forward together with the coupling shaft (122) when the plunger (120) is pressed and to contract to an original length and apply elastic force to the plunger (120) so that the plunger (120) is moved backward by the reference distance when pressure applied to the plunger (120) is released.

2. The syringe according to claim 1, wherein the gasket coupling ring (130) comprises:

a ring body (131) fitted on the coupling shaft (122);

a rear flange (135) protruding from an outer circumference of a rear end of the ring body (131) and spaced apart from the front pressing plate (121) by the reference distance; and a front flange (133) protruding from an outer circumference of a front end of the ring body (131) to a lower height than the rear flange (135) and forming a band fitting groove (137) into which the fixing band (141) is fitted between the front flange (133) and the rear flange (135), and wherein the coupling shaft (122) is provided with a movement limiting protrusion (123) protruding therefrom so as to be in contact with the front flange (133) to limit forward movement of the gasket coupling ring (130).

3. The syringe according to claim 2, wherein the tip cap (145) is formed to have a length allowing the front end of the coupling shaft (122) to be exposed to an outside, and wherein the syringe further comprises a tip separation preventing protrusion (124) provided in a coupling region between the tip cap (145) and the coupling shaft (122) so as to fix a position of the tip cap (145).

* * * * *